US011276566B2

(12) United States Patent
Yamaguchi

(10) Patent No.: US 11,276,566 B2
(45) Date of Patent: Mar. 15, 2022

(54) IMAGING DATA PROCESSING DEVICE

(71) Applicant: SHIMADZU CORPORATION, Kyoto (JP)

(72) Inventor: Shinichi Yamaguchi, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 0 days.

(21) Appl. No.: 17/055,808

(22) PCT Filed: May 30, 2018

(86) PCT No.: PCT/JP2018/020836
§ 371 (c)(1),
(2) Date: Nov. 16, 2020

(87) PCT Pub. No.: WO2019/229900
PCT Pub. Date: Dec. 5, 2019

(65) Prior Publication Data
US 2021/0210318 A1      Jul. 8, 2021

(51) Int. Cl.
*H01J 49/00* (2006.01)
*G01N 27/62* (2021.01)
(Continued)

(52) U.S. Cl.
CPC ......... *H01J 49/0036* (2013.01); *G01N 27/62* (2013.01); *G01N 33/483* (2013.01); *H01J 49/0004* (2013.01); *H01J 49/26* (2013.01)

(58) Field of Classification Search
CPC .... H01J 49/0036; H01J 49/0004; H01J 49/26; G01N 27/62; G01N 33/483
(Continued)

(56) References Cited

U.S. PATENT DOCUMENTS

2018/0197726 A1* 7/2018 Yamaguchi ............ G16B 40/30

FOREIGN PATENT DOCUMENTS

| WO | 2017/002226 A1 | 1/2017 | |
| WO | WO-2017002226 A1 * | 1/2017 | ............ G16B 40/30 |
| WO | 2019/150573 A1 | 8/2019 | |

OTHER PUBLICATIONS

Van de Plas, et al ("Fusion of mass spectrometry and microscopy: a multi-modality paradigm for molecular tissue mapping," Nature Methods, Apr. 2015, pp. 366-372, vol. 12, No. 4) (Year: 2015).*

(Continued)

*Primary Examiner* — Michael Maskell
(74) *Attorney, Agent, or Firm* — Sughrue Mion, PLLC

(57) ABSTRACT

An image creator (33) creates an optical image and a mass spectrometric (MS) image for each m/z for a measurement area on the same sample, and an image alignment processor (34) equalizes resolutions and aligns the images. A regression analysis executer (35) performs partial least squares regression (PLS) to create a regression model, using a matrix based on the MS imaging data as an explanatory variable and a matrix, which has a luminance value for each pixel as an element and has been created from the optical image, as an explained variable. An image creator (33) applies the explanatory variable, that is, a signal intensity value for each mass-to-charge ratio value in each pixel of the MS imaging data, to the regression model to create an estimation image. A display processor (39) displays a reference image and the estimation image on a screen of a display unit (5). Thus, an operator can confirm the degree of similarity in distribution between the MS image and the optical image. Consequently, the accuracy of the created regression model can be evaluated.

8 Claims, 2 Drawing Sheets

(51) Int. Cl.
*G01N 33/483* (2006.01)
*H01J 49/26* (2006.01)

(58) Field of Classification Search
USPC .............................. 250/281, 282; 702/27–32
See application file for complete search history.

(56) References Cited

OTHER PUBLICATIONS

"iMScope TRIO Imaging Mass Microscope," [online], [Searched on Mar. 28, 2018], Shimadzu Corporation, Internet URL:https://www.an.shimadzu.co.jp/bio/imscope/, with its corresponding English pages, 1-5 pages.

Raf Van De Plas, et al, "Image fusion of mass spectrometry and microscopy: a multimodality paradigm for molecular tissue mapping", Nature Methods, Apr. 2015, pp. 366-372, vol. 12, No. 4.

Andreas Römpp, et al., "Mass spectrometry imaging with high resolution in mass and space", Histochem Cell Biol, 2013, pp. 759-783, vol. 139, issue 6.

International Search Report for PCT/JP2018/020836 dated Aug. 28, 2018 [PCT/ISA/210].

Written Opinion for PCT/JP2018/020836 dated Aug. 28, 2018 [PCT/ISA/237].

\* cited by examiner

IMAGING DATA PROCESSING DEVICE

CROSS REFERENCE TO RELATED APPLICATIONS

This application is a National Stage of International Application No. PCT/JP2018/020836 filed May 30, 2018.

TECHNICAL FIELD

The present invention relates to an imaging data processing device which can create an image showing a two-dimensional distribution of a specific substance in a sample and extract useful information on the sample by processing data obtained in each of many minute areas in a two-dimensional measurement area on the sample by an imaging mass spectrometer or the like.

BACKGROUND ART

An imaging mass spectrometer is a device capable of obtaining a two-dimensional intensity distribution of ions having a specific mass-to-charge ratio m/z on the surface of a sample such as a piece of biological tissue, while observing the surface morphology of the same sample with an optical microscope (cf. Non Patent Literature 1). By using the imaging mass spectrometer to observe a two-dimensional intensity distribution image (mass spectrometric image) of ions derived from a compound characteristically appearing in a specific disease such as cancer, it is possible to grasp the extent of the disease. For this reason, in recent years, studies have been actively conducted using imaging mass spectrometers to analyze the pharmacokinetics of a piece of biological tissue or the like or analyze the difference in the distribution of a compound in organs, the difference in the distribution of a compound between a pathological site of a cancer or the like and a normal site, or the like.

In general, the two-dimensional intensity distribution of ions having a certain mass-to-charge ratio shows the distribution of a specific substance, so that it is possible to obtain useful information on the basis of a mass spectrometric image, such as how a compound related to a specific disease, that is, a biomarker, is distributed in a biological tissue. However, the amount of data obtained in the imaging mass spectrometer is enormous, and when the type of compound to be observed is unknown, it takes a great deal of labor for an operator to examine at which mass-to-charge ratio the information of a mass spectrometric image is useful.

In order to solve these problems, Patent Literature 1 describes that image alignment and spatial resolution adjustment are performed between a reference image, such as an optical image or a fluorescent image obtained by an optical microscope, and a mass spectrometric image at an arbitrary mass-to-charge ratio, and then statistical analysis processing is performed on data between corresponding pixels in both images to calculate an index value showing the similarity in distribution between both images. The literature also describes the use of regression analysis, such as Partial Least Squares Regression (PLS), as a statistical analysis method. In this method, the higher the correlation between the two-dimensional distribution of the mass spectrometric image and the reference image, the higher the PLS score, so that it is possible to estimate that ions with a mass-to-charge ratio which gives a high-score mass spectrometric image have a two-dimensional intensity distribution close to the reference image. Such information is important in search for a biomarker.

PCT/JP2018/003757, filed by the present applicant, describes that PLS regression analysis is performed using a two-dimensional matrix, created from mass spectrometric imaging data within a predetermined mass-to-charge ratio range collected for a sample, as an explanatory variable, and using a one-dimensional matrix, created from pixel value data of a reference image, as an explained variable (target variable) to obtain a one-dimensional matrix of a regression coefficient, and from the obtained result, a spectrum-like graph showing the relationship between the mass-to-charge ratio and the regression coefficient is created and displayed. A mass-to-charge ratio having a large absolute value of the regression coefficient can be seen at a glance on this graph, so that the operator can easily find a mass-to-charge ratio showing a two-dimensional intensity distribution close to the reference image.

CITATION LIST

Patent Literature

Patent Literature 1: WO 2017/002226 A

Non Patent Literature

Non Patent Literature 1: "iMScope TRIO Imaging Mass Microscope," [online], [Searched on Mar. 28, 2018], Shimadzu Corporation, Internet

SUMMARY OF INVENTION

Technical Problem

As described above, by comparing PLS scores (regression coefficients) obtained from mass spectrometric images at different mass-to-charge ratios, it is possible to make a relative determination at which mass-to-charge ratio the mass spectrometric image is closer to the reference image. However, even with such a score, it is not possible to make an absolute determination of how much degree the mass spectrometric image at a given mass-to-charge ratio is similar to the reference image. Therefore, even when the scores, obtained from mass spectrometric images at a plurality of mass-to-charge ratios different from each other and one reference image, are compared to extract one mass-to-charge ratio having the highest score, there is no guarantee that the similarity in two-dimensional distribution between the mass to charge image at that mass-to-charge ratio and the reference image is sufficiently high.

Generally, in PLS, a calculated value called a determination coefficient (also called a contribution rate) is often used as an index value showing the similarity of a PLS model (regression equation). In order to calculate the determination coefficient, it is necessary to obtain three values: a total variation, a regression variation, and a residual variation from each actual data set and its regression equation, and to calculate the determination coefficient from those values for all actual data sets. However, in the case of mass spectrometric imaging, the amount of data to be processed is extremely large, and hence it is practically impossible to calculate the determination coefficient.

Note that similar problems are common to mass spectrometric imaging and imaging by various measurement methods such as Raman spectroscopic imaging, fluorescence imaging, and infrared spectroscopic imaging.

The present invention has been made to solve these problems, and it is an object of the present invention to provide an imaging data processing device which enables a user to instantly and easily grasp the degree of similarity between a mass spectrometric image and an optical image in the same measurement area, for example, when the similarity is examined by statistical analysis processing.

Solution to Problem

The present invention, which has been made to solve the above problems, is an imaging data processing device for obtaining information on a sample by a data analysis processing on measurement image data and reference imaging data, where the measurement image data is a collection of data obtained by a predetermined measurement method of acquiring a spectrum for each of minute areas in a two-dimensional measurement area on the sample, and the reference imaging data is that constitutes a reference image which is a two-dimensional distribution of intensity information for each of the minute areas on the sample, the imaging data processing device including:

a) a regression analysis executer configured to perform regression analysis, using first imaging data as an explanatory variable and second imaging data as an explained variable (target variable) to create regression model, the first imaging data being all or a part of the measurement imaging data, the second imaging data being all or a part of the reference imaging data spatially corresponding to the first imaging data; and b) an estimation image creator configured to apply the first imaging data to the regression model to create an estimation image based on a regression analysis result.

In the present invention, the predetermined measurement method may be any of mass spectrometric imaging, Raman spectroscopic imaging, fluorescence imaging, infrared spectroscopic imaging, and X-ray analytical imaging. Further, the reference image can be an image obtained by performing a measurement on a sample by one of measurement methods different from one selected as the predetermined measurement method in measurement methods including surface analytical imaging using a particle beam such as an electron beam or an ion beam, surface analytical imaging using a probe such as a scanning probe microscope (SPM), and microscopic observation using a general microscope such as an optical microscope as well as the above-mentioned measurement methods. Here, the reference image is an image to be used as a reference at the time of evaluating an image based on the measurement imaging data. Hence the measurement imaging data need not be an image obtained for the same sample as the acquired sample. Further, the measurement imaging data may be an image artificially created without depending on the measurement.

In a typical embodiment of the present invention, the predetermined measurement method is a mass spectrometry method, and the measurement imaging data is mass spectral data within a predetermined mass-to-charge ratio range in each pixel.

As an example, it is assumed that the measurement imaging data is mass spectrometric imaging data obtained for a measurement area on one sample as described above and that the reference imaging data is image data constituting an optical image for the measurement area on the same sample. In the present invention, the regression analysis executer performs regression analysis using mass spectrometric imaging data of the entire measurement area as an explanatory variable and image data constituting an optical image for the entire measurement area as an explained variable (target variable) and obtains a regression coefficient for each mass-to-charge ratio to create a regression model. Then, the estimation image creator applies mass spectrometric imaging data, which is an explanatory variable, to the regression model and creates an estimation image based on the regression analysis result. In this case, it is desirable to use partial least squares regression analysis as the regression analysis instead of general multiple regression.

According to a first aspect of the present invention, the imaging data processing device may further include a residual image creator configured to calculate an estimation residual for each of the minute areas on the basis of the estimation image, create a residual image, and display the residual image on a screen of a display unit.

In a regression model, when the element (regression coefficient) is capable of complete regression, the estimation residual becomes zero in all pixels, but in practice, there is almost always an error in regression, and hence the estimation residual occurs. Since the estimation residual reflects the accuracy of the regression model, the user can evaluate the accuracy of the regression model by confirming the residual image.

According to a second aspect of the present invention, the imaging data processing device may further include an analysis result image creator configured to display both the estimation image and the reference image on the screen of the display unit.

When the accuracy of the regression model obtained by the regression analysis is high, the two-dimensional distributions of the estimation image as the regression analysis result and the reference image become close to each other. Therefore, the user can evaluate the accuracy of the regression model by comparing the estimation image and the reference image displayed side by side on the screen of the display unit.

According to a third aspect of the present invention, the imaging data processing device may further include: a correlation coefficient calculator configured to calculate a correlation coefficient showing a correlation in pixels spatially corresponding between the estimation image and the reference image; and a display processor configured to display the correlation coefficient calculated by the correlation coefficient calculator on the screen of the display unit.

As described above, when the accuracy of the regression model is high, the two-dimensional distributions of the estimation image and the reference image become close to each other, so that the correlation coefficient of both images becomes large. Therefore, the user can evaluate the accuracy of the regression model by confirming the correlation coefficient.

According to a fourth aspect of the present invention, the imaging data processing device may further include: a regression analysis result evaluator configured to subtract or divide a pixel value for each of pixels spatially corresponding between the estimation image and the reference image to calculate a calculated value; and a difference image creator configured to create an image based on the calculated value for each of the pixels calculated by the regression analysis result evaluator and display the image on the screen of the display unit.

When the accuracy of the regression model is high, the two-dimensional distributions of the estimation image and the reference image become close to each other, so that the calculated value obtained by subtracting or dividing the pixel values of both images becomes close to a constant value. Therefore, the user can evaluate the accuracy of the regression model by confirming the image based on the calculated value.

In the imaging data processing device according to the present invention, when the measurement imaging data is mass spectrometric imaging data as described above, it is preferable that in the measurement imaging data, a signal intensity in a range within a degree of device accuracy of a used mass spectrometer for each of peaks in a profile spectrum obtained by mass spectrometry be integrated and taken as a signal intensity of the peak.

Generally, the peak width of the peak observed in the profile spectrum is larger than the mass-to-charge ratio width determined by the device accuracy and resolution of the mass spectrometer. This is caused by various errors in repeated measurements for the same site on the same sample. Due to the spread of the peak as thus described, when the signal intensity is integrated with respect to the whole (range from start to end) of one peak detected on the profile spectrum, the accuracy of the signal intensity deteriorates because it is affected by a tail portion of another peak or some other reason. In contrast, with the above preferred configuration, it is possible to reduce the influence of such errors and create a highly accurate mass spectrometric image.

Advantageous Effects of Invention

According to the present invention, using a regression model created from optical image data as an explanatory variable and mass spectrometric imaging data as an explained variable, an estimation image close to the optical image can be created, and the accuracy of the regression analysis result can be evaluated based on that. Thus, the work of searching for a biomarker can be made efficient.

DESCRIPTION OF EMBODIMENTS

An embodiment of an imaging mass spectrometer using an imaging data processing device according to the present invention will be described with reference to the accompanying drawings.

Figure 1:
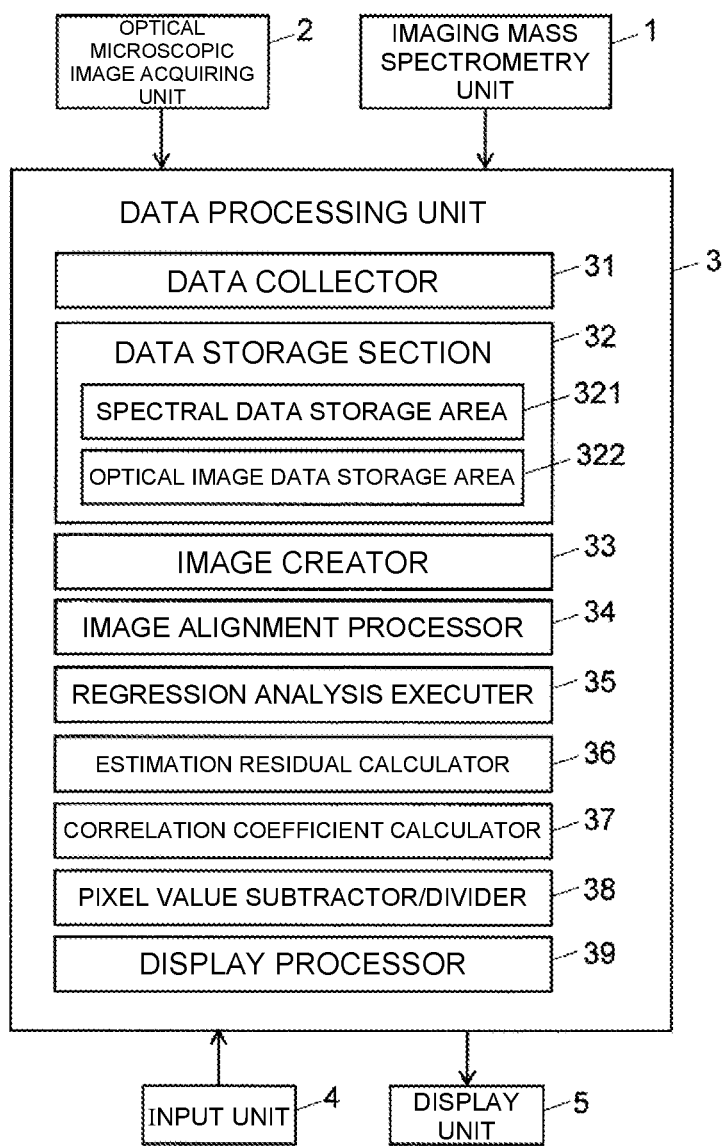
FIG. 1 is a schematic block diagram of an embodiment of an imaging mass spectrometer including an imaging data processing device according to the present invention.

FIG. 1 is a schematic block diagram of an imaging mass spectrometer of the present embodiment. The device includes an imaging mass spectrometry unit 1 for performing a measurement on a sample by a mass spectrometric imaging, an optical microscopic image acquiring unit 2 for taking an optical image on the sample, a data processing unit 3, and an input unit 4 and a display unit 5 which are user interfaces.

The imaging mass spectrometry unit 1 includes, for example, a matrix-assisted laser desorption/ionization (MALDI) ion trap time-of-flight mass spectrometer, and performs mass spectrometry on many measurement points (minute areas) in a two-dimensional measurement area on a sample such as a piece of biological tissue to acquire mass spectrometric data for each minute area. Here, the mass spectrometric data is mass spectral data within a predetermined mass-to-charge ratio range, but may be $MS^n$ spectral data for a specific precursor ion. The optical microscopic image acquiring unit 2 is formed by adding an image acquiring unit to an optical microscope and acquires an optical image of a two-dimensional area of the surface on a sample.

The data processing unit 3 receives the mass spectral data in each minute area collected by the imaging mass spectrometry unit 1 and the optical microscopic image data input from the optical microscopic image acquiring unit 2 and performs predetermined processing. The data processing unit 3 includes, as functional blocks, a data collector 31, a data storage section 32, an image creator 33, an image alignment processor 34, a regression analysis executer 35, an estimation residual calculator 36, a correlation coefficient calculator 37, a pixel value subtractor/divider 38, a display processor 39, and the like. The data storage section 32 includes a spectral data storage area 321 for storing data collected by measurement by the imaging mass spectrometry unit 1, and an optical image data storage area 322 for storing image data collected by measurement (imaging) by the optical microscopic image acquiring unit 2.

Note that the substance of the data processing unit 3 is usually a personal computer (higher-performance workstation), and the function of each of the above functional blocks can be achieved by operating, on the computer, dedicated software installed on the computer. In this case, the input unit 4 is a pointing device such as a keyboard or a mouse, and the display unit 5 is a display monitor.

Next, the work of measuring a sample in the device of the present embodiment will be described.

First, when an operator sets a target sample at a predetermined measurement position of the optical microscopic image acquiring unit 2 and performs a predetermined operation with the input unit 4, the optical microscopic image acquiring unit 2 takes an image of the surface of the sample and stores optical image data in the optical image data storage area 322. The image creator 33 creates an optical image, and the display processor 39 displays the image on the screen of the display unit 5. The operator instructs the whole sample or a measurement area, which is a part of the sample, on the image with an input unit 4.

The operator takes out a sample once and attaches a matrix for MALDI to the surface of the sample. Then, the sample to which the matrix is attached is set at a predetermined measurement position of the imaging mass spectrometry unit 1, and a predetermined operation is performed by the input unit 4. Thus, the imaging mass spectrometry unit 1 performs mass spectrometry on many minute areas in the measurement area instructed as described above on the sample, and acquires mass spectrometric data within a predetermined mass-to-charge ratio range. At this time, the data collector 31 performs so-called profile acquisition, collects profile spectral data, which is a waveform continuous in the direction of the mass-to-charge ratio within the mass-to-charge ratio range, and stores the collected data into the spectral data storage area 321 of the data storage section 32.

In a case where a pattern (boundaries of different organizations, etc.) on the sample surface can be observed relatively clearly even when the matrix is attached to the sample surface, the imaging may be performed by the optical microscopic image acquiring unit 2 after the matrix is attached to the sample surface.

While the mass spectrometric imaging data and the optical image data for the sample are stored in the data storage section 32 described above, the data processing is performed as follows.

In the data processing unit 3, the image creator 33 reads profile data on one sample to be processed from the spectral data storage area 321 of the data storage section 32, calculates signal intensities at a plurality of predetermined target mass-to-charge ratios for each minute area, and creates a mass spectrometric image showing a two-dimensional distribution of signal intensities for each mass-to-charge ratio.

Figure 2:
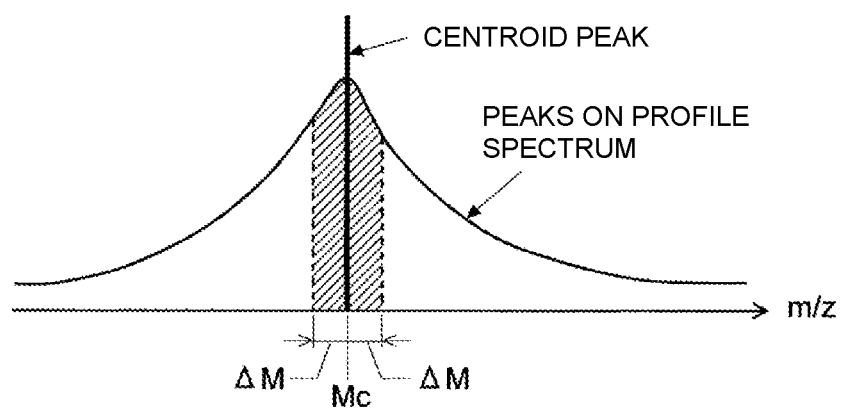
FIG. 2 is a diagram showing the relationship between a peak on a profile spectrum and an intensity integration range.

Specifically, as shown in FIG. 2, a profile spectrum is created from the profile data, a peak is detected on the profile spectrum, and centroid conversion processing is performed on each detected peak to obtain an accurate peak position (mass-to-charge ratio value) Mc. When the mass-to-charge ratio value Mc of the centroid peak is within a predetermined mass-to-charge ratio range with the specified mass-to-charge ratio as the center, the centroid peak is regarded as a peak corresponding to the target mass-to-charge ratio. Then, signal intensity values within a predetermined mass-to-charge ratio range (the range of the mass accuracy degree of the mass spectrometer) Mc±ΔM with the centroid peak as the center in the profile spectrum is integrated to obtain a signal intensity value with respect to the target mass-to-charge ratio. The two-dimensional distribution of the signal intensity value at the target mass-to-charge ratio can be obtained by performing similar processing on the profile data in each minute area, so that the mass spectrometric image at one target mass-to-charge ratio can be obtained by imaging the obtained two-dimensional distribution.

The image creator 33 reads the optical image data on the same sample from the optical image data storage area 322 of the data storage section 32 and creates one optical image. In general, the spatial resolution of the optical microscopic image acquiring unit 2 is usually determined by the resolution of an imaging camera, while the resolution of the mass spectrometric image is determined by the spot diameter of a laser beam applied onto the sample for ionization. Hence the resolution of mass spectrometric images is often lower than the resolution of the optical image. Therefore, when the spatial resolution of the optical image is different from that of the mass spectrometric image, the image alignment processor 34 performs resolution adjustment processing to equalize the spatial resolutions.

A simple method of equalizing the resolutions is a method of reducing the resolution of an image with higher resolution to match an image with lower resolution. As such a method, for example, binning processing is useful. The resolution of the image with lower resolution may be increased to match the image with higher resolution. For this purpose, up-sampling processing is performed on the image with lower resolution to apparently match the number of pixels, and thereafter, a pixel value of a pixel newly inserted by the up-sampling is calculated and filled by interpolation processing using a plurality of pixel values adjacent to or close to a certain pixel.

After the spatial resolution is equalized, the image alignment processor 34 appropriately deforms the optical image so that the positions of the mass spectrometric image and the optical image are approximately equalized in pixel units. Specifically, for example, the mass spectrometric image is enlarged, reduced, rotated, moved, and further deformed in accordance with a predetermined algorithm with respect to the optical image as a reference, so that the positional relationship between the two images on the sample is matched approximately. By such processing, pixels at the same two-dimensional positions can be corresponded between the optical image and the mass spectrometric image. The optical image processed in this manner is used as a reference image. The optical image may not be used as it is, but a two-dimensional distribution image of a luminance value of a specific color component instructed by the operator, the image having been created by extracting the color component from the optical image, may be used as a reference image as disclosed in Patent Literature 1 and the like.

Figure 3:
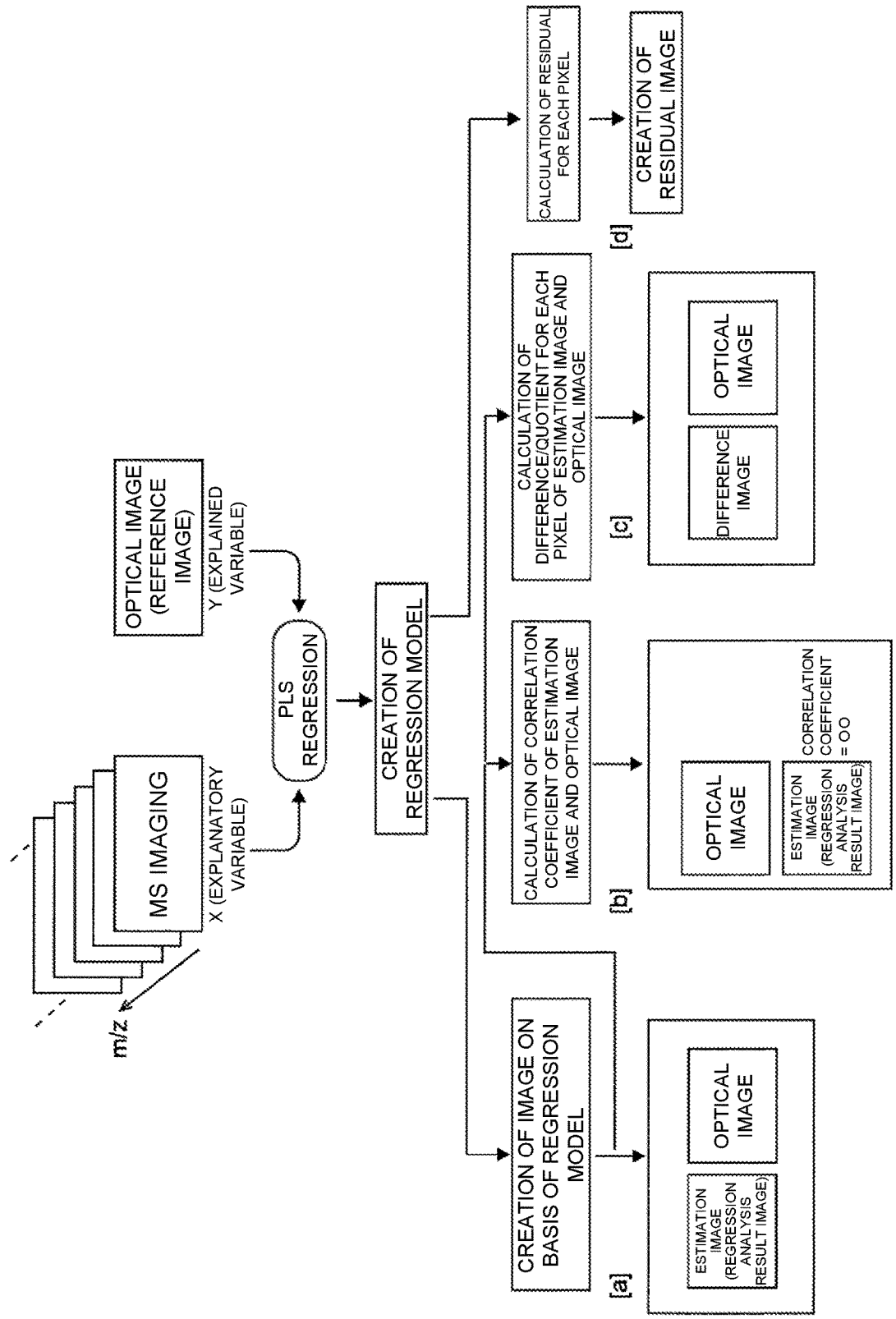
FIG. 3 is an explanatory diagram of data processing in the imaging mass spectrometer of the present embodiment.

Then, the regression analysis executer 35 performs PLS, using as an explanatory variable (X) a matrix which has a signal intensity value for each mass-to-charge ratio value in each pixel as an element and has been created from mass spectrometric imaging data constituting the mass spectrometric image after the processing, and using as an explained variable (Y) a matrix which has a luminance value for each pixel as an element and has also been created from the reference image. Then, an image similar to the two-dimensional distribution of the reference image, that is, a regression model (regression equation) is created from the signal intensity value of the mass spectrometric imaging data for each mass-to-charge ratio (cf. FIG. 3). As is well known, the regression model in PLS is represented by Y=Bpis■X+B$_0$. Bpis is a matrix of regression coefficients. PLS can be calculated using a variety of commonly available software.

According to the device of the present embodiment, various pieces of information obtained from the regression model can be selectively provided to the operator in accordance with the operator's specification.

(1) Display of Estimation Image as Regression Analysis Result Based on Regression Model When the regression model is obtained, the image creator 33 applies an explanatory variable, that is, a signal intensity value for each mass-to-charge ratio value in each pixel of the mass spectrometric imaging data, to the regression model to create an estimation image based on the regression analysis result. When the accuracy of the regression model is high, that is, when the regression model can well explain the explained variable on the basis of the explanatory variable, the two-dimensional distribution of the estimation image is similar to the two-dimensional distribution of the reference image. Therefore, as shown in [a] in FIG. 3, the display processor 39 causes the display unit 5 to display one estimation image and the reference image in the screen in a side-by-side arranged manner. Naturally, in addition to the arrangement, one of the images may be made semitransparent and displayed in an overlapping manner.

By such a display, the operator can compare the reference image with the estimation image, visually confirm whether the distributions are indeed similar, and evaluate the accuracy of the created regression model. Thereby, a mass-to-charge ratio similar in distribution to the reference image can be selected as a candidate biomarker.

(2) Display of Correlation Coefficient between Estimation Image and Reference Image When the regression model is obtained, the image creator 33 applies an explanatory variable, that is, a signal intensity value for each mass-to-charge ratio value in each pixel of the mass spectrometric imaging data, to the regression model to create an estimation image based on the regression analysis result. The correlation coefficient calculator 37 calculates a correlation coefficient in pixel units for the estimation image and the reference image. Thus, a correlation coefficient reflecting the similarity of the two-dimensional distribution with the reference image is obtained for each estimation image. As shown in [b] in FIG. 3, the display processor 39 causes the display unit 5 to display, for example, the estimation image and the correlation coefficient. In this case, the reference image may also be displayed.

By such a display, the operator can confirm whether the two-dimensional distributions of the estimation image and the reference image are similar on the basis of the numerical value of the correlation coefficient, and evaluate the accuracy of the created regression model. Thereby, a mass-to-charge ratio similar in distribution to the reference image can be selected as a candidate biomarker.

(3) Display of Image by Subtraction/Division for Estimation Image and Reference Image When the regression model is obtained, the image creator 33 applies an explanatory variable, that is, a signal intensity value for each mass-to-charge ratio value in each pixel of the mass spectrometric imaging data, to the regression model to create an estimation image based on the regression analysis result. The pixel value subtractor/divider 38 standardizes each pixel value in the estimation image and each pixel value in the reference image to roughly equalize the pixel values. For example, the following methods are conceivable: a method of calculating the average value of all pixel values for each image and normalizing each pixel value such that the average value becomes the same, or a method of normalizing each pixel value such that the maximum pixel value among all pixel values in each image becomes the same. Note that the normalization of the pixel value is not essential.

After the pixel values are normalized, the difference between the pixel values of one image and the pixel values of the other image is calculated in pixel units. Alternatively, the division may be performed in pixel units to obtain the quotient of the pixel values. Thus, the pixel values are subtracted or divided for each pixel, and when a calculated value as the result of the subtraction or division is determined, the image creator 33 creates an image based on the calculated value. As shown in [c] in FIG. 3, the display processor 39 causes the display unit 5 to display the image of the calculated value (difference image in FIG. 3).

When the similarity between the two-dimensional distributions of the reference image and the estimation image is high, the pixel value of the image based on the subtraction or division is close to constant. Thus, by such a display as described above, the operator can confirm whether the two-dimensional distributions of the estimation image and the reference image are similar and evaluate the accuracy of the created regression model. Thereby, a mass-to-charge ratio similar in distribution to the reference image can be selected as a candidate biomarker.

(4) Display of Estimation Residual Image Based on Regression Model

When the regression model is obtained, the image creator 33 applies an explanatory variable, that is, a signal intensity value for each mass-to-charge ratio value in each pixel of the mass spectrometric imaging data, to the regression model to create an estimation image based on the regression analysis result. The estimation residual calculator 36 calculates an estimation residual for each pixel on the basis of the estimation image. This estimation residual can be calculated by a known method in regression analysis such as PLS. This estimation residual is a small value in the pixel in which the regression is performed with high accuracy. The image creator 33 creates an image based on the estimation residual. As shown in [d] in FIG. 3, the display processor 39 causes the display unit 5 to display the created estimation residual image.

When the similarity between the two-dimensional distribution of the reference image and the estimation image is high, the residual image is in a nearly constant state. Thus, by such a display as described above, the operator can visually confirm the residual image to determine whether the two-dimensional distributions of the estimation image and the reference image are similar and evaluate the accuracy of the created regression model. Thereby, a mass-to-charge ratio similar in distribution to the reference image can be selected as a candidate biomarker.

As described above, in the imaging mass spectrometer of the present embodiment, the operator can find a mass image having a two-dimensional distribution truly similar to that of the reference image and extract a mass-to-charge ratio corresponding to the image as a candidate biomarker by using various displays made by characteristic data processing.

Although the imaging mass spectrometer of the above embodiment has used the optical image as the reference image, the reference image may be an image obtained by other measurement methods except for the mass spectrometric imaging for the same sample, for example, Raman spectroscopic imaging, infrared spectroscopic imaging, X-ray analytical imaging, surface analytical imaging using a particle beam such as an electron beam or an ion beam, or surface analytical imaging using a probe such as a scanning probe microscope (SPM). The reference image is not necessarily required to be an image obtained for the same sample, and for example, even different samples may be treated as substantially the same sample so long as the samples are adjacent piece samples in continuous piece samples formed by slicing a biological tissue into very thin pieces. In such a case, a mass spectrometric image and a reference image may be obtained for different samples, respectively, which can be considered as the same sample.

The present invention can also be applied to a case where the similarity between the image data obtained by various kinds of imaging as described above and the optical image data or the like is examined, rather than the data obtained by the mass spectrometric imaging.

Further, the above embodiment is merely an example of the present invention, and it is natural that, even when modification, correction, and addition are made as appropriate in the scope of the gist of the present invention in addition to the various modifications described above, those are included in the scope of claims of the present invention.

REFERENCE SIGNS LIST

1 . . . Imaging Mass Spectrometry Unit
2 . . . Optical Microscopic Image Acquiring Unit
22 . . . Data Storage Section
3 . . . Data Processing Unit
31 . . . Data Collector
32 . . . Data Storage Section
321 . . . Spectral Data Storage Area
322 . . . Optical Image Data Storage Area
33 . . . Image Creator
34 . . . Image Alignment Processor
35 . . . Regression Analysis Executer
36 . . . Estimation Residual Calculator
37 . . . Correlation Coefficient Calculator
38 . . . Pixel Value Subtractor/Divider
39 . . . Display Processor
4 . . . Input Unit
5 . . . Display Unit

The invention claimed is:

1. An imaging data processing device for obtaining information on a sample by a data analysis processing on measurement image data and reference imaging data, where the measurement image data is a collection of data obtained by a predetermined measurement method of acquiring a spectrum for each of minute areas in a two-dimensional measurement area on the sample, and the reference imaging data is that constitutes a reference image which is a two-dimensional distribution of intensity information for each of the minute areas on the sample, the imaging data processing device comprising:
- a) a regression analysis executer configured to perform regression analysis, using first imaging data as an explanatory variable and second imaging data as an explained variable to create regression model, the first imaging data being all or a part of the measurement imaging data, the second imaging data being all or a part of the reference imaging data spatially corresponding to the first imaging data; and
- b) an estimation image creator configured to apply the first imaging data to the regression model to create an estimation image based on a regression analysis result.

2. The imaging data processing device according to claim 1, further comprising
a residual image creator configured to calculate an estimation residual for each of the minute areas on a basis of the estimation image, create a residual image, and display the residual image on a screen of a display unit.

3. The imaging data processing device according to claim 1, further comprising
an analysis result image creator configured to display both the estimation image and the reference image on a screen of a display unit.

4. The imaging data processing device according to claim 1, further comprising:
a correlation coefficient calculator configured to calculate a correlation coefficient showing a correlation in pixels spatially corresponding between the estimation image and the reference image; and
a display processor configured to display a correlation coefficient calculated by the correlation coefficient calculator on a screen of a display unit.

5. The imaging data processing device according to claim 1, further comprising:
a regression analysis result evaluator configured to subtract or divide a pixel value for each of pixels spatially corresponding between the estimation image and the reference image to calculate a calculated value; and
a difference image creator configured to create an image based on the calculated value for each of the pixels calculated by the regression analysis result evaluator and display an image on a screen of a display unit.

6. The imaging data processing device according to claim 1, wherein
the predetermined measurement method is a mass spectrometry method, and
in the measurement imaging data, a signal intensity in a range within a degree of device accuracy of a used mass spectrometer for each of peaks in a profile spectrum obtained by mass spectrometry is integrated and taken as a signal intensity of the peak.

7. The imaging data processing device according to claim 1, wherein the regression analysis is a partial least squares regression analysis.

8. The imaging data processing device according to claim 6, wherein the regression analysis is a partial least squares regression analysis.

\* \* \* \* \*